(12) United States Patent
Dodgson et al.

(10) Patent No.: US 6,454,923 B1
(45) Date of Patent: *Sep. 24, 2002

(54) GAS SENSOR

(75) Inventors: John Dodgson, Croydon (GB); John Edward Andrew Shaw, West Drayton (GB); Malcolm Austen, Hayes (GB); Monica Backes, Ealing (GB)

(73) Assignee: Central Research Laboratories Limited, Hayes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/554,129

(22) PCT Filed: Nov. 10, 1998

(86) PCT No.: PCT/GB98/03363

§ 371 (c)(1),
(2), (4) Date: Jun. 23, 2000

(87) PCT Pub. No.: WO99/24826

PCT Pub. Date: May 20, 1999

(51) Int. Cl.[7] .............................................. G01N 27/404
(52) U.S. Cl. ...................... 204/415; 204/401; 204/412; 205/783
(58) Field of Search ................................. 204/415, 412, 204/401

(56) References Cited

U.S. PATENT DOCUMENTS

| 4,100,048 | A | * | 7/1978 | Pompei |
| 4,141,800 | A | * | 2/1979 | Breuer et al. |
| RE31,915 | E | * | 6/1985 | Oswin et al. |
| 5,183,550 | A | | 2/1993 | Mattiessen |
| 5,302,274 | A | * | 4/1994 | Tomantschger et al. |
| 5,741,413 | A | * | 4/1998 | Capetanopoulos |
| 5,830,337 | A | * | 11/1998 | Xu |
| 5,980,709 | A | * | 11/1999 | Hodges et al. |

FOREIGN PATENT DOCUMENTS

| EP | 0301897 A2 | 2/1988 |
| EP | 0744620 A1 | 11/1996 |
| GB | 2067764 A | 7/1981 |
| GB | 2254696 A | 10/1992 |
| WO | WO 96/14576 | 5/1996 |

* cited by examiner

Primary Examiner—T. Tung
(74) Attorney, Agent, or Firm—William H. Bollman

(57) ABSTRACT

A gas sensor is described which is particularly well suited as a carbon monoxide (CO) sensor in a self test gas sensor. The sensor includes a number of aspects which may or may not be used in conjunction with one another. A first aspect is an embodiment which reduces electrical interference (or crosstalk) between a test or gas generating cell and a sensing cell. In one embodiment, baffles are provided to prevent crosstalk. In another embodiment a switching circuit ensures that a test gas generator is operational only when the gas sensor is disconnected from a current source. A second aspect is an embodiment which includes an improved wick which is in close proximity with an electrode and ensures electrolyte is always in contact with the electrode. In an alternate embodiment a solid polymer electrolyte is used between the electrodes. A third aspect is an improved catalyst which reduces the reaction energy and thereby renders the sensor more sensitive. The catalyst is also cheaper than platinum. Overall the gas sensor uses less components than existing gas sensors and is therefore cheaper and easier to assemble and more reliable.

28 Claims, 10 Drawing Sheets

GAS SENSOR

The present invention relates to gas sensors, and more particularly, but not exclusively to gas sensors incorporating a self-test capability. These types of gas sensors are hereinafter referred to as self-test gas sensors. The invention is suitable for use in electrochemical gas sensors, such as, for example, carbon monoxide (CO) sensors.

Conventional electrochemical gas sensors for use in CO sensors, operate by oxidizing a gas to be detected at a sensing electrode, thereby generating an electric current. The rate of access to the sensing electrode may be determined by a diffusion barrier, and the rate at which the electrode is capable of oxidizing the gas is arranged to be very much greater than the rate at which the gas can diffuse through the barrier. Generally the rate of oxidation, and hence the electric current generated, is controlled mainly by diffusion. This diffusion rate has a value (for a given gas concentration) and the sensor can be calibrated when it is manufactured. If the activicty of the sensing electrode falls with time, e.g., through poisoning, then the level of current generated eventually becomes limited by a lower oxidation rate. This results in a decrease in sensitivity of the sensor. There is then no way of determining, from the sensor output alone, whether the gas concentration is low, or whether the gas concentration is high and the electrode has lost activity become less sensitive.

Previously, so as to overcome this problem, the sensitivity of sensors was ascertained by regular tests involving exposure to a calibration gas of known concentration. In many situations, for example in a domestic carbon monoxide safety monitor, this was undesirable.

In the Applicant's published International Patent Application WO-A-9703372, the contents of which are incorporated herein by way of reference, there is described a self-test gas sensor having electrolytic gas generation electrodes and sensor electrodes being located in close proximity one to the other within the same housing. The aforementioned gas sensor has several advantages over previous gas sensors, including lower operating power, as the amount of gas needed to be generated for the self test procedure is reduced; and lower assembly costs, as the test and sensing cells are effectively assembled in the same operation. The self-test gas sensor operates by generating locally a small volume of gas (hereinafter referred to as a "test gas") and detecting the test gas in the sensor, thereby confirming the status of the sensor, i.e. functioning or faulty.

It is desirable that the response of the gas sensor, during the self test procedure, should result only from the response of the sensor to the test gas generated during that procedure, and not arise from electrical interference which may occur between the sensor and gas generator circuits as a result of electrochemical reactions.

According to the present invention there is provided a self-test gas sensor comprising: a sensor for sensing a gas and a test cell, the test cell being arranged to generate a test gas on demand, and a test gas pathway for directing the test gas to the gas sensor so that generated test gas is detected by the gas sensor, thereby verifying that the gas sensor is functioning, characterised in that a baffle is disposed between the gas sensor and the test cell so as to prevent electrical interference therebetween.

Sensing electrodes are electrically isolated from test cell electrodes by way of the baffle. Preferably the baffle is situated in a fluid pathway between the sensing circuit and the test circuit. The baffle prevents flow of ions (and therefore electric current) between what is effectively a test cell and a gas sensor cell when the test cell is operating. The baffle may comprise two or more portions. The first portion preferably comprises a gas impermeable substrate, and the second portion comprises a gas permeable substrate. The gas permeable substrate of the baffle permits the passage of water vapour between the test cell and the gas sensor. The gas permeable substrate helps to maintain electrolyte, present in the gas sensor, at a substantially constant pH and/or concentration.

A further requirement is that the complexity of the sensor and gas generator cells, and their respective operating circuits, should be minimised in order to reduce unit costs.

According to another aspect of the invention a self test gas sensor includes first, second and third electrodes, the first electrode being a common electrode, the second electrode in operation with the first electrode, acting as a pair to generate a test gas; the third electrode in operation with the first electrode acting as gas sensor, characterized in that means is provided to isolate test and sensing electrodes one from another, so that only one pair of electrodes is operational at any instant.

It is also envisaged that an embodiment of the sensor having three electrodes is within the scope of the present invention, a counter electrode being common to a test and a sensing electrode. In this embodiment electrical interference or cross-talk between components is avoided by ensuring the sensing and test components operate at different instants. Cross talk between the two sets of electrodes is avoided by a switch which ensures that the test electrode and reference electrode are only energized when the sensing electrode is switched out of circuit. Clearly in an embodiment where there is a common electrolyte there is a risk of cross talk between two (or more) pairs of electrodes and switching one pair out of circuit whilst a separate pair are switched in circuit is one way of avoiding this.

Preferably a capacitive element is provided for storing energy from an energy source which supplies electric current to a pair of sensing electrodes during operation of the sensor, there being a switch arranged to disconnect the supply of electric current to the sensing electrodes and connect the capacitive element to the test electrodes thereby providing an independent source of current thereto.

In normal sensing use, the capacitive element is changed from the sensing circuit power supply. In test mode, the capacitor is isolated from the power supply by a switch, and connected to the test electrode circuit, so as to discharge through the test circuit and generate gas at the test electrode. The capacitor provides a supply isolated from the sensor circuit supply, and so the generation current will not flow through the sensor electrodes, provided also that a baffle as aforementioned is in place between the test electrode and sensing electrode.

Preferably the sensor and the test cell are disposed within a housing, which permits gas from the environment to pass to the gas sensor via a gas pathway. The gas pathway is preferably separated from a test gas pathway.

Preferably the electrically conductive pathways by-pass the or each baffle thereby further reducing the risk of interference between a test circuit and a sensing circuit.

There may be a counter electrode common to the sensor and the test cell. The sensor electrodes and the test cell electrodes may be formed on a gas permeable membrane, such as PTFE.

Strengthening ribs may be incorporated into the body of the housing. A diffusion barrier may be provided to limit the rate of arrival of a gas at the gas sensor.

UK Patent Application GB-A-2323171 (City Technology Limited) discloses a sensor in which electrical contact to an internal electrode is made, via an electrical connector, from an external terminal. The electrical connection is made between the electrical connector and the external terminal by forcing electrically conductive components together under pressure and maintaining the pressure throughout the working life of the sensor. It is believed that such connections eventually fail, not as a result of relaxation of the compression of components, but rather as a result of relaxation or perishing of either intervening gaskets or O-ring seals;

A further advantage of the present invention, over the arrangement described in GB-A2323171, is the fact that relatively few components are present compared to the arrangement shown in FIG. 1 of GB-A-2323171. This feature makes the present invention cheaper and easier to manufacture. Also, because less components are present there is less risk that the sensor will fail. This is particularly important when considering the working life of the sensor may be several years.

According to a different aspect of the present invention there is provided a self test gas sensor comprising a housing, which is hermetically sealed from an external atmosphere apart from at least one entrance, through which a gas to be sensed may pass, which sensor. in use contains an electrolyte in contact with a sensing electrode, a counter electrode and a test electrode, there being a wick interposed between the sensing and counter electrodes, the wick being dimensioned and arranged so as to supply electrolyte to both electrodes irrespective of the orientation of the sensor, and electrically conductive pathways provided which contact the counter and sensing electrodes and pass to electrical terminals supported on an external surface of the housing.

A filter means may also be provided, the filter means prevents unwanted substances, such as ethanol ($C_2H_5OH$), from contacting the sensor. The filter means may include a charcoal filter.

When a test gas is generated by the test cell, it passes to a recessed volume, from where it passes to the gas sensor. The recessed volume, may be situated in the housing. Most preferably, gas generated by the test cell passes to the gas sensor via a gas permeable membrane. The gas permeable membrane may be made of PTFE. The sensor electrodes and the test cell electrodes may be formed on a gas permeable membrane, such as PTFE.

The sensor and the test cell have an electrolyte so that, in use, an electrochemical reaction is supported between two test electrodes, and between the sensor electrodes. Means may be provided for maintaining the electrolyte in contact with the electrodes. The sensor and the test cell are preferably in fluid communication one with another, so that when the self-test gas sensor is in use, electrolyte may flow freely from the sensor to the test cell.

Electrodes are preferably operated by a potentiostat circuit. Separate voltage sources may be used to operate the test cell electrodes and the sensor cell electrodes. At least one reference electrode may be provided in contact with the electrolyte for use in the sensing circuit.

A barrier may be provided to prevent gas from the atmosphere from contacting the reference electrode via the recessed volume. The barrier may be formed integrally with the housing.

In many electrochemical processes it is advantageous to design an electrochemical cell so that electrolyte remains in intimate contact with electrodes, in varying conditions of orientation and movement of the cell and differing concentrations of electrolyte. This is especially so when the electrolyte volume varies with time and so occupies a varying proportion of a space between two or more electrodes, or between an electrode and an ambient atmosphere. This change in volume of electrolyte can give rise to variation in the effective area of electrodes which are in contact with the electrolyte. This area of contact should be maximised, or at least vary to the least degree possible.

A particular example of an electrochemical cell where the aforementioned problem has been experienced is in gas sensors. Gas sensors need to operate in any orientation so that the electrolyte concentration remains in equilibrium with the humidity of the atmosphere. Variation in volume and in effective area of contact in the manner previously described is therefore undesirable.

Various methods of overcoming the aforementioned problem exist for gas sensors. Examples include gelled electrolytes, which adhere to the surface of electrodes; solid polymer electrolytes, such as NAFION (Trade Mark); which can be cast onto or impregnated into the electrode surface; and wicks which are held against the surface of an electrode using physical pressure. All these however, suffer from disadvantages. Gelled electrolytes have a volume and consistency which often varies considerably with concentration, and so can flow from the electrode surface in high humidity atmospheres, solidifying elsewhere when the humidity falls again Solid polymer electrolytes remain in place, but are expensive, have a conductivity that varies strongly with humidity and so need liquid acid in contact with them. Also they can be difficult to apply sparingly to the electrode surface in high volume production. Wicks are cheap and effective, but careful mechanical design is needed to ensure that they remain in good physical contact with the electrode in any orientation and under conditions where the cell might suffer shock or impact. Also, in certain types of electrochemical cell, it is necessary to ensure that the electrode surface is entirely covered with electrolyte in order to prevent gas access to that surface. To ensure this using only physical pressure on a wick is difficult.

According to another aspect of the present invention there is provided an electrode assembly comprising a porous structure in contact with an electrode, the porous structure being arranged to adhere to the electrode so that in use the structure is in contact with an electrolyte, thereby continuously wetting substantially all the surface of the electrode with electrolyte.

Preferably the porous structure includes a wick material. The porous structure is preferably deposited onto a support substrate, which may be the electrode, in a liquid or paste-like form, for example by screen printing, thereby fabricating the electrode assembly. Fabrication is then completed by one or more of: drying, setting, sintering or pressing the porous structure adjacent the electrode so as to define the electrode assembly.

In a preferred embodiment a thin layer of wick material of fibrous or bound porous particular material is placed upon onto a wet deposited electrode surface and urged into a top layer of the electrode. Then using post-processing (for example by one or more of heat, pressure and drying), the wick material becomes firmly and uniformly attached to the electrode surface in such a way as to ensure uniform distribution of electrolyte over the surface without disrupting the bulk of the electrode structure. Thus electrical conductivity is ensured, the electrochemical efficiency of the electrode is unaltered and the porous structure is capable of supporting efficient transfer of liquid by capillary action.

The porous structure is advantageously dimensioned and arranged so that it comprises different layers or regions of differing porosity, so that layers close to the surface of the electrode have a greater affinity to the electrolyte than those layers further from the electrode surface. This enhances capillary action and improves the wicking effect, thus ensuring the electrode surface is always wetted by electrolyte.

An additional advantage, which may be of importance in certain sensors, is that gas diffusion electrodes need to maintain hydrophobicity through their bulk to maximize their reaction efficiency. Portions of the surface of the electrode assembly may be substantially hydrophobic, with some small hydrophilic areas. Generally electrodes have an hydrophilic surface in order to provide high surface area for reactions to proceed. The introduction of an hydrophilic wick material into the electrode assembly assists this process.

Preferably the porous wick material is sinteied onto the electrode at a temperature between 300° C. to 370° C. and most preferably within a temperature range between 320° C. to 370° C. The exact temperature depends upon the nature of ink printed onto the electrode and the substrate.

The electrode assembly may be incorporated into an electrochemical cell or a gas sensor, which may or may not be a self test gas sensor as herein before described.

Conventional electrochemical gas sensors comprise at least three electrodes, namely a sensing electrode, a reference electrode and a counter electrode, located within a housing containing electrolyte. The housing usually has a diffusion barrier in the form of a small aperture through which ambient gases can diffuse to contact the sensing electrode. The ambient gas are oxidized by the sensing electrode thereby generating an electrical current indicative of the concentration of oxidized gases. The rate of access of the ambient gas to the sensing electrode is determined by the design of the diffusion barrier and the rate at which the electrode can oxidize the ambient gases is arranged to be very much greater than the rate at which the gas diffuses through the barrier. Therefore the rate of oxidation of the gases, and hence the current generated, is controlled solely by the rate of diffusion, (and this is a known value for each sensor for a given gas concentration), when the sensor is manufactured. If the activity of the sensing electrode falls with time, for example, due to poisoning, then the current generated becomes limited by the lower oxidation rate at the sensing electrode and the sensitivity of the sensor falls. The sensor is not fail safe. There is no way of telling from the cell output whether the gas concentration is low, or that the concentration is higher and the sensing electrode has lost actvity.

Reliability of such sensors can be ascertained by regular tests involving exposure of the sensor to an external calibration gas. In many situations, for example, in a domestic CO safety monitor, this is not practical and is undesirable. To overcome this shortfall, it is known to construct sensors with a self-test ability which may be triggered remotely or locally.

GB-A-1 552 538 (Bayer) describes a self-test sensor assembly consisting of two parts, a sensor and a gas generation means, for example an electrolysis cell, joined by a delivery channel. Test gas is delivered directly to the sensing electrode of the sensor, with a membrane between the point of gas delivery and the outside world. Delivery is by a piston, a pressure difference resulting from the generation of gas itself, or other means. Signal gas enters the sensor from the atmosphere via the membrane. In this arrangement the concentration of test gas seen by the sensing electrode depends on the balance of the rate of generation of the gas and the rate of loss through the membrane—the latter depends on the conditions (air flow) outside the membrane. As the generator is remote from the sensing electrode, there is a large volume to be filled with gas in order to ensure that a consistent known concentration is reached. This means the design is likely to require significant power, which is a limitation of the use of such a principle in a low power domestic monitor circuit.

GB-A-2 245 711 describes a gas sensor with solid electrolyte layers disposed on two sets of electrodes, one designed for a gas sensing function, and the other set provided for a test function. The test function electrodes are arranged to sense a gas normally present in the atmosphere, e.g., oxygen. A decrease in the signal from the test electrodes is taken to indicate a either a decrease in activity of the test electrodes, or a decrease in the permeability of the solid electrolyte, through which test and signal gas must pass before they reach the electrodes. Such change in permeability is a major factor in the performance of the sensor type disclosed in GB-A-2 245 711. The test of electrode decay rests on the assumption that the test electrodes will decay in the same way as the sensing electrodes. The test reaction uses oxygen ($O_2$) and is fundamentally different from the sensing reaction for oxidizing gases, being a reduction rather than an oxidation reaction, and so this form of test is likely to prove unreliable. A test where the sensing electrodes oxidizes test gas generated in known quantity, as in GB-A-1 552 538 would be advantageous.

The Applicants Co-pending UK Patent Application No 9625463 discloses a self-test gas sensor including a housing containing at least a sensing electrode, a counter electrode and a test electrode. The sensor has the sensing and counter electrodes in a first electrolyte and the test electrode in a second electrolyte. Gas from the environment flows to the sensing electrode through a diffuser passage. In operation in a normal mode of operation, electrical potentials are applied to the electrodes for detecting when a gas to be sensed is present at the sensing electrode. In a test mode of operation, electrical potentials are applied to the electrodes so that the test electrode generates a gas which flows to the sensing electrode to enable an indication whether the sensor is operating correctly.

According to a yet further aspect of the present invention there is provided a sensor comprising a housing in which there is located a sensing electrode, a counter electrode, a reference electrode and electrolyte in contact with the electrodes, said housing having a diffusion barrier through which ambient gas to be detected may pass, the cell being operable in a sensing mode, where electrical potentials are applied to the counter electrode and the sensing electrode, to effect reaction of ambient gases that reach the sensing electrode and thereby produce an electrical current indicative of the concentration of the gas to be detected, characterised in that the sensing electrode comprises an electrically conductive layer deposited on a first gas permeable substrate, said counter electrode and the reference electrode each comprise an electrically conductive layer deposited on a surface of the second gas permeable substrate which faces towards the sensing electrode, and a gas permeable wick which in use conveys electrolyte to the said electrodes is positioned between the substrates in contact with the electrodes.

A cheap and accurate means is provided of self-testing, wherein the test gas is generated within of the sensor and in a controlled amount by application of a suitable voltage potential.

The proposed self-test electrochemical cell described in the Applicant's UK Patent Application No 9625461 includes a planar arrangement of one or more sensing electrodes and one or more electrolytic gas generator electrodes in the same housing in contact with common or separate electrolytes, with associated counter and reference electrodes. The gas generating electrodes are located close to the sensing electrode or electrodes, so as to minimise the amount of gas that is needed to be generated to effect a test of the operation of the sensor. In one embodiment described in our aforementioned UK Patent Application the test gas Hydrogen $H_2$ is delivered to the sensing electrode in the gas phase, by evolution into a communicating space above the electrodes. The test gas generated by the generator electrode is $H_2$ which is generated by the reaction:

$$2H^+ + 2e \rightarrow H_2(gas) \qquad (Eqn\ 1)$$

It is a feature of this reaction that, if the generation electrode has a source of oxygen available, then oxygen will be reduced also:

$$\tfrac{1}{2}O_2 + 2H^+ + 2e \rightarrow H_2O \qquad (Eqn\ 2)$$

which passes a current in parallel with that passed in the $H_2$ generation reaction, and so reduces the operating efficiency of the generator. Oxygen reduction reaction occurs particularly advantageously if the generator electrode is permeable and in contact with the atmosphere. Conventionally, the gas generator electrode is made of a material which is an active catalyst for the generation of $H_2$ such as for example platinum, and the electrical current generated at the sensing electrode as a result of the reduction of oxygen will be large compared with that generated as a result of hydrogen generation at low electrode potentials.

The electrochemical performance, meanwhile, benefits in that the electrochemical potential of the electrodes responds similarly to changes in temperature, humidity and poisoning, so keeping the background signal to a minimum. However, such a construction suffers from two disadvantages. Firstly, all three electrodes contain costly, highly active, noble metal catalyst, such as platinum. Secondly the potential of the reference electrode responds to exposure to an analyte gas, and must be isolated from incoming gas. This is currently achieved by a "reverse seal", a process which heat scals the area between the reference and working electrodes to the diffusion barrier below. This operation can be difficult to carry out reliably, and, more significantly, prevents the cell housings being built from only two pieces.

According to a further aspect of the present invention there is provided a gas sensor comprising: a sensory cell having at least one sensing electrode, a counter electrode, a sensory circuit; a test cell comprising at least a generating electrode, a counter electrode and a test circuit, the sensor being arranged so that in use an electrolyte is in contact with the electrodes, there being a membrane, through which gas may pass to the sensing electrode; the gas sensor being capable of operation in either a sensing mode, or in a test mode, characterised in that at least the generating electrode is coated with a catalyst for improving the efficiency of generation of a test gas.

The efficiency of the generation of hydrogen test gas is improved by making the gas generation electrode from a material which is a poor catalyst for the reduction of oxygen.

Preferably the catalyst comprises ruthenium dioxide and the test gas generated is hydrogen. The catalyst may be applied to the electrode(s) in the form of an ink. The invention provides a cheap and accurate means of enabling production of a high quality, efficient electrodes for use in a gas sensor.

Preferably electrodes are planar. One or more sensing electrodes and one or more generation electrodes may be enclosed in the same housing, in contact with common or separate electrolytes, with associated counter and reference electrodes as required by an embodiment, so that gas generation electrodes are close to sensing electrodes. This minimises the amount of gas that is need to effect the test. In one embodiment the test gas is delivered to the sensing electrode in the gas phase, by evolution into a communicating space above the electrodes.

In a preferred embodiment test gas to be generated is hydrogen and is generated by the reaction described in Eqn 1. It is a feature of this reaction that, if the generation electrode has a source of oxygen available, then oxygen will be reduced according to Eqn 2. It is apparent from Eqn 2 that electric current flows in parallel with that passed in the generation reaction described in Eqn 1, and so reduces the operating efficiency of the generator. The oxygen reduction reaction occurs if the generation electrode is permeable and in contact with the atmosphere. If the electrode is of an active catalyst such as those conventionally used in electrochemical sensors, for example platinum, the oxygen reduction current will be large compared with the hydrogen generation current at low electrode potentials. In the counter and reference electrodes alternative materials to platinum may be used.

Where the counter electrode is replaced, the alternative material requires a degree of catalytic activity such that it is able to perform the counter reaction without any loss of response of the overall cell. For example, in a cell which detects carbon monoxide by oxidation at its sensing electrode, oxygen is reduced at the counter electrode. Materials which are proposed for this purpose are gold, ruthenium oxide and carbon.

In the situation where the reference electrode is replaced with an alternative material, the requirement for the material is that its electrochemical potential is stable with time and that it varies in response to changes in temperature and humidity by a similar amount to the sensing electrode. Similar materials to the above are suggested as replacements for the noble metal catalyst.

The invention has significant worth if it is applied to cells which contain a self test function. In the manufacture of such cells, a second electrode print is required to produce the self test gas production electrodes. At least one of the self test electrodes must be a poor oxygen reduction electrode such that hydrogen is evolved in preference to other reactions. Suitable materials for these electrodes are again, ruthenium oxide, gold and carbon. Thus if a single material from this list can satisfy the requirements for the self test, counter and reference electrodes, significant reduction in catalyst expense can be achieved without adding a further screen printing stage.

Use of electrode materials for gas generation electrode(s) different to those used for sensing electrodes helps to improve the overall efficiency. The generation electrode is advantageously a poor catalyst for oxygen reduction. An example is (Ruthenium Dioxide), which is highly conductive, is easily dispersed in ink, and generates hydrogen in the presence of oxygen at a much lower electropotentials (i.e. lower total current density) than may be platinum. Other materials which are also poor oxygen reduction catalysts may be used.

The electrode membrane is preferably a double print, with the sensing and reference areas of the membrane in platinum ink, and the generator electrodes and the sensor counter electrode(s) in ruthenium dioxide ink. Ruthenium dioxide ink may also be used as a conductive support layer to the platinum ink in order to increase conductivity and reduce cost.

Different aspects of the invention have been described and those are illustrated below by way of examples. However, it is understood that although some aspects are illustrated independently one from another, an embodiment incorporating two or more of the aspects described is envisaged within the scope of this description. That is to say for, example the aspect of the invention which includes baffles for reducing electrical cross-talk, may also have a capacitive energy storage circuit and electrodes with ruthenium dioxide catalyst. Similarly after combinations of features may be combined to provide a superior self test gas sensor.

In order to reduce oxygen access to the generator electrode if a membrane with a single print of platinum or other active oxygen reduction catalyst is preferred, the porosity of the membrane above the generation electrode may be reduced, but not to such a degree as to inhibit excessively the exit of hydrogen gas. This can be achieved, for example, by hot-pressing the membrane in the area of the generation electrode, by partially impregnating the area with PTFE or a similar impervious substance, or by sealing (either partially or completely) a low porosity material over the membrane. Alternatively, access of oxygen may he inhibited, while allowing hydrogen to exhaust from the sensor, by ensuring the exit through which hydrogen exhausts is narrow.

Embodiments of the invention will now be described, by way of examples only, and with reference to the Figures, in which.

Figure 1:
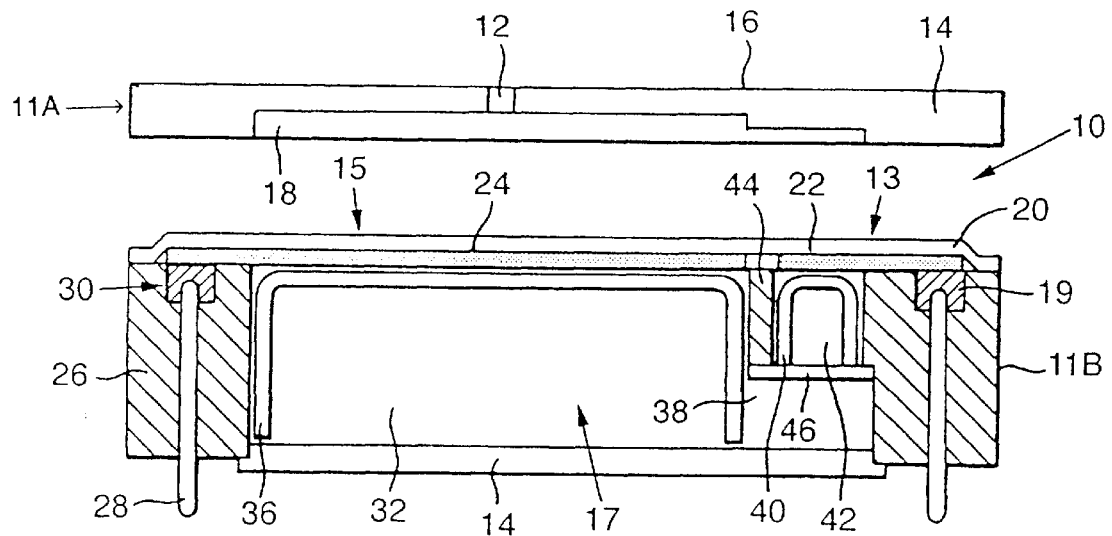
FIG. 1 is a sectional view of a gas sensor employing an embodiment of the invention.
Figure 9:
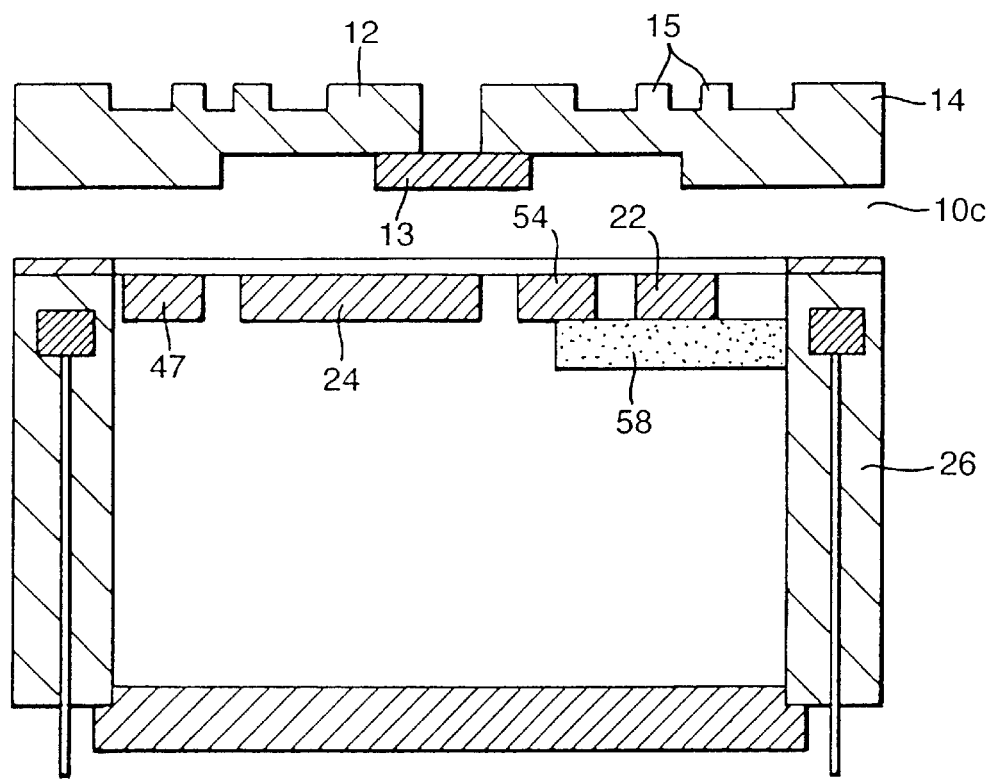
Figure 10:
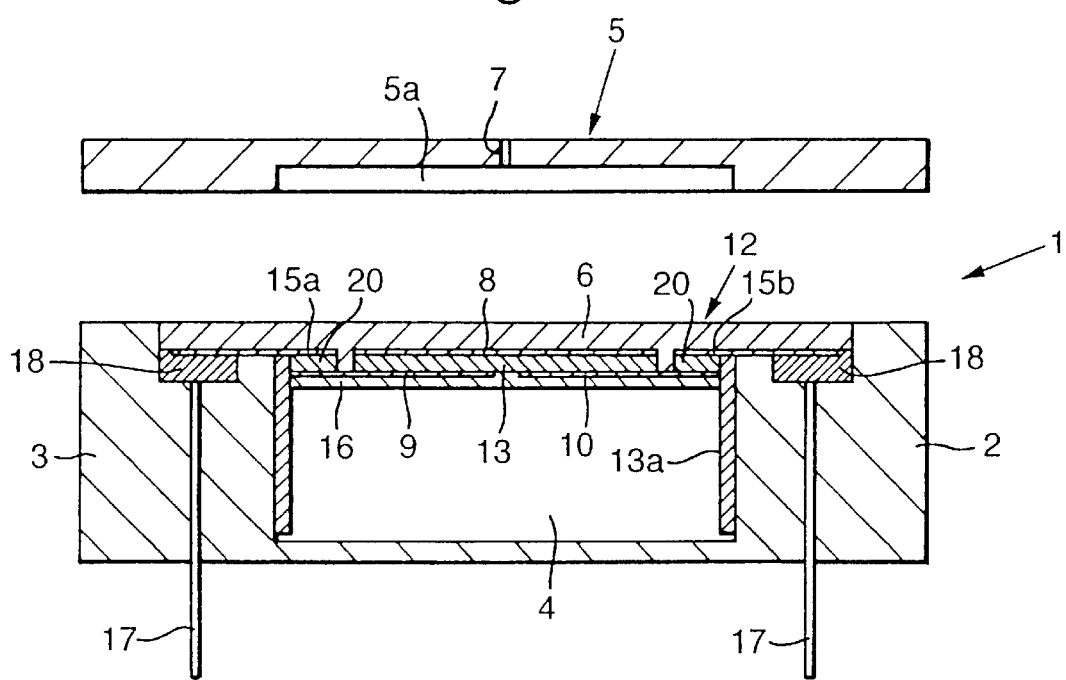
Figure 11:
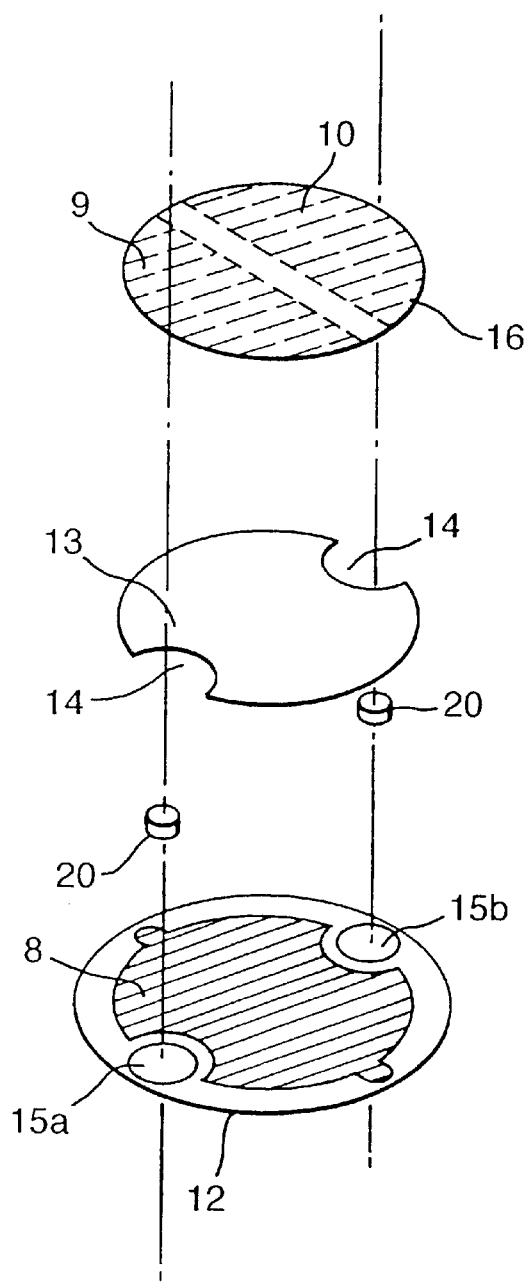
Figure 12:
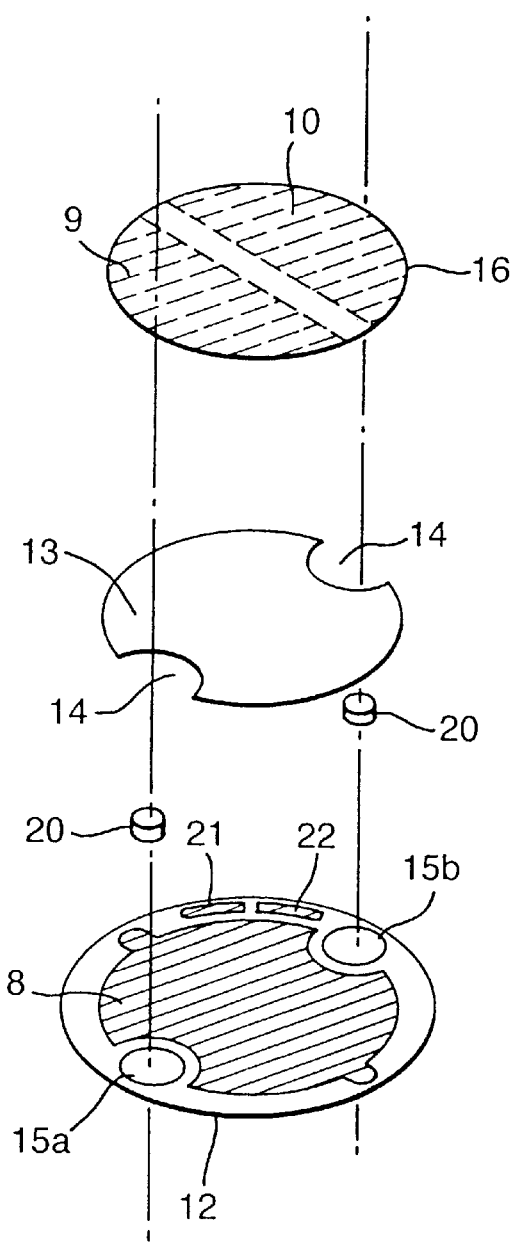
Figure 13:
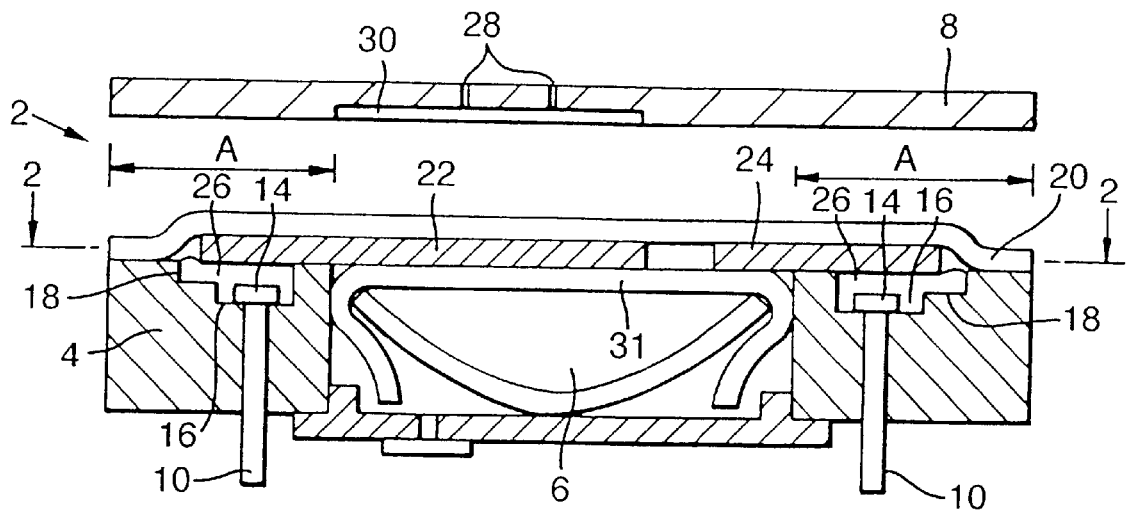
Figure 14:
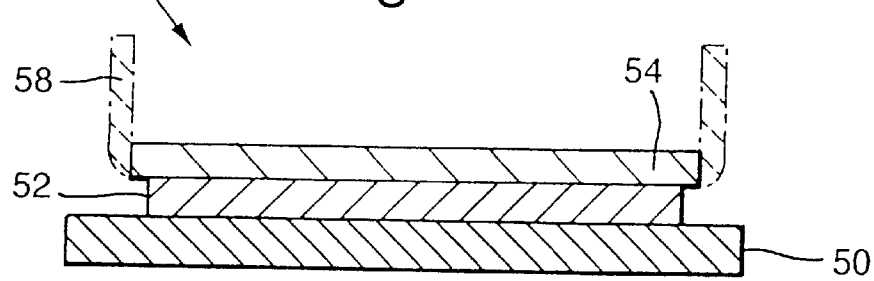
Figure 15:
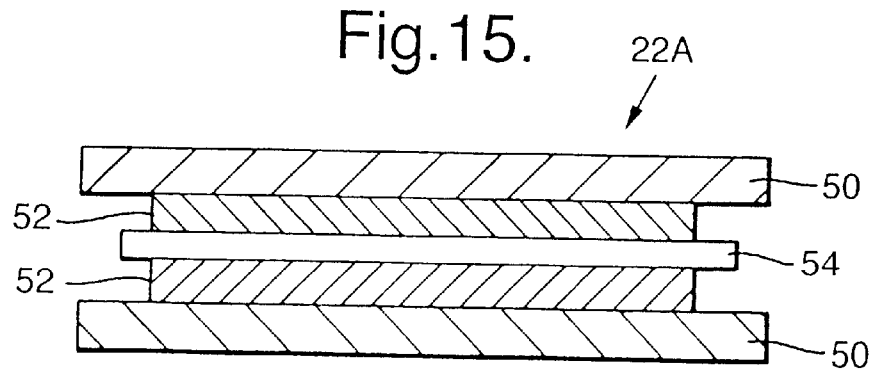

FIGS. 4, 4A, 5, 5A, 6, 6A, 7, 7A 8 and 8A are schematic circuit diagrams for use in the sensor of FIGS. 1 and 9;

FIG. 9 is a sectional view of an alternative embodiment of a sensor employing the invention;

FIG. 10 is a cross-sectional view of embodiment of a gas sensor incorporating an electrode assembly of the type shown in FIG. 11;

FIG. 11 is an exploded view of an embodiment of an electrode assembly comprising two substrates with intervening wick;

FIG. 12 is an alternative embodiment to that shown in FIG. 11 having two test electrodes;

FIG. 13 shows a cross-sectional view of a further embodiment of a gas sensor which incorporates one or more aspects of the present invention;

FIG. 14 is a view of an example of the electrode assembly of the sensor shown in FIG. 13; and FIG. 15 illustrates a further embodiment of the electrode assembly shown in FIG. 14.

Referring to FIG. 1, this shows the construction of a self test gas sensor 10. Sensor 10 comprises a two-part housing 11A and B, a test cell 13 and a sensor portion or sensor cell 15. The two-part housing 11 comprises a housing body 26 with a hollow interior 17, which together define an electrolyte reservoir 32. A cap member 14 seals the said reservoir 28. Electrical contact pins 2, of nickel or tinned copper, are located in recesses 30 in the housing body 26. A conductive polymer/carbon composite 19 is placed in recesses 30 over the head of each contact pin 28.

Cap member 14 has a diffusion barrier 12, leading to a recessed manifold area 18. Gas from the atmosphere diffuses through barrier 12 via a charcoal filter (not shown), to the manifold area 18. Atmospheric gas subsequently passes through flexible membrane 20 to sensing electrode 24. The rate of arrival of atmospheric gas at sensing electrode 24 is governed by the diffusion barrier 12.

On operation of the sensor, gas from the environment passes through diffusion barrier 12 to manifold 18. If the gas to be sensed is carbon monoxide, an electrochemical reaction is created at sensor electrode 24 on contact between the electrolyte and the gas. An electrochemical reaction also occurs at the counter electrode 48 with oxygen from the atmosphere. Current is carried through the electrolytic solution by ions produced in the reactions, and by electrons in an external circuit. The current in the external circuit indicates the concentration of carbon monoxide in the atmosphere.

Figure 2:
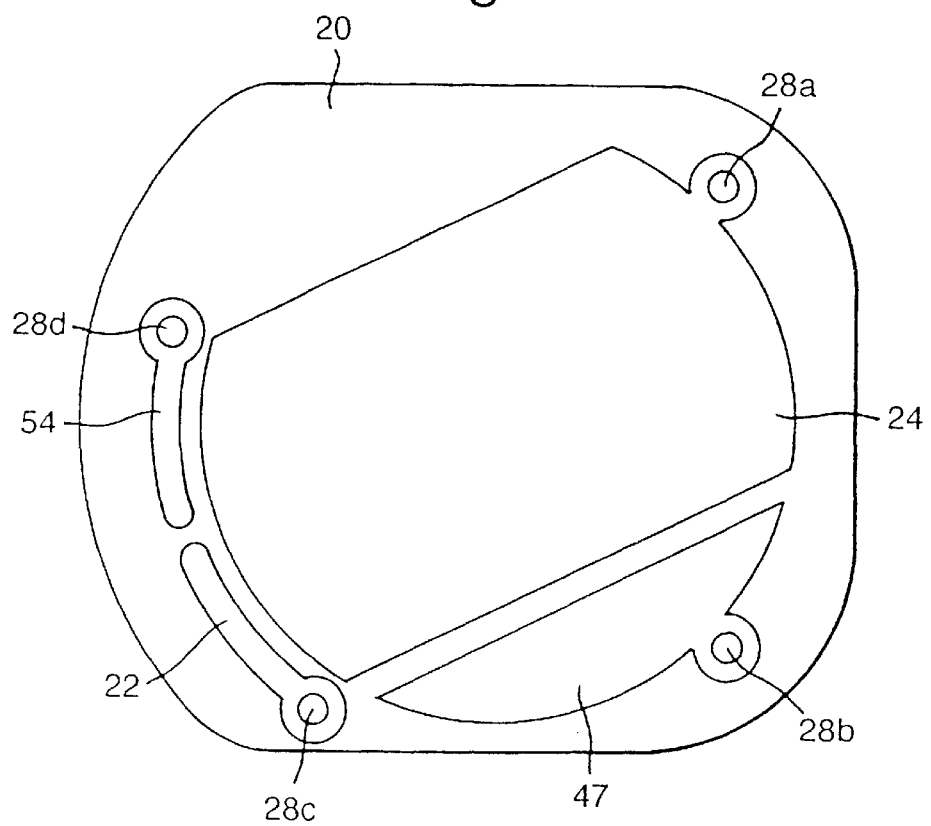
FIGS. 2, 2A and 3 are plan views of electrode configurations for use in the sensor shown in FIG. 1.
Figure 2A:
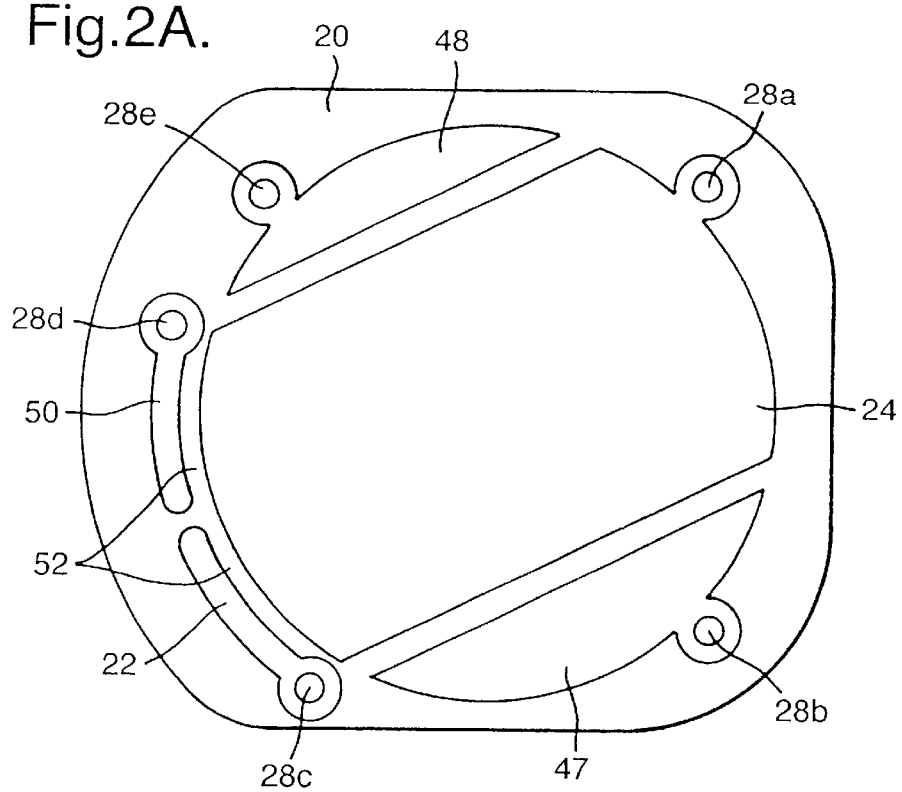
Figure 3:
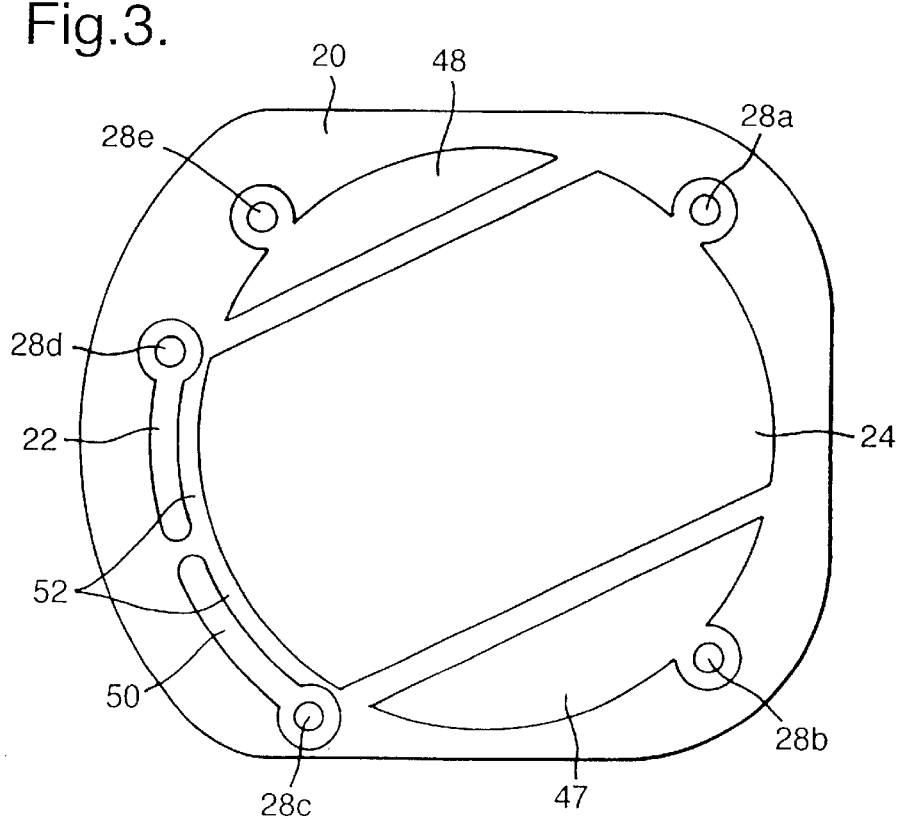

Referring now to FIG. 2A and 3 there are shown views of an electrode configuration which may be employed with the structure of FIG. 1. Similar parts are denoted by the same reference numeral. A sensing, electrode 24 occupies the central region of membrane 20, and is coupled at its right hand end to a terminal pin 28a. A reference electrode 47 is located adjacent the sensor electrode and is coupled at its right hand end to a terminal pin 28b. A counter electrode 48 is located on the opposite side of the sensor electrode 24 to the reference electrode 47, and is coupled at its left hand end to a terminal pin 28e. A test electrode 22 and counter electrode 50 are separated from the sensing electrode 24 by a narrow channel 52. Test electrode 22 and counter electrode 50 are connected to respective electrical contact pins 28c and 28d. In FIG. 2, the counter electrode 48 is omitted, and test cell counter electrode 54 serves as a counter electrode for the sensor cell also.

Flexible membrane 20 has hydrophobic and microporous regions disposed on an upper surface thereof. Membrane 20 may be formed from Polytetrafluoroethene (PTFE). Test cell electrode 22, and sensor electrodes 24 and 47, are screen printed or filter deposited onto the lower surface of 20. Electrode 47, the reference electrode, is maintained at a stable potential by way of a barrier which prevents gas from the atmosphere contacting the electrode via recessed manifold 18.

Electrodes 22, 24 and 47 are formed from a mixture of electrically conductive catalyst particles such as, for example, platinum or ruthenium oxide and a PTFE binder. Sensing electrode 24 and test electrode 22 may be separated by the inclusion of a barrier, or baffle, 44 and 46. (FIG. 1) Baffle 44, 46 comprises an impermeable barrier 44, and a porous membrane 46. Impermeable barrier 44 and porous membrane 46 together define a volume 42 within the test cell 13. Barrier 44 extends in a perpendicular direction from membrane 20 towards base region of body part 26. Porous membrane 46 acts as a lid and encloses chamber 42. Porous membrane 46 allows passage of water vapour and a test gas between chambers 32 & 42. Thus increase of pressure inside the sensor is avoided.

In use, electrolyte (not shown), within electrolyte reservoir 32, is maintained in contact with electrodes 24 and 47 by means of a wick 36. Electrolyte 8 within volume 42 is maintained in contact with electrode 22 by wick 40. The electrolyte employed is an aqueous solution, for example including sulphuric acid ($H_2SO_4$), so that hydrogen gas ($H_2$) is generated as the test gas, and oxygen ($O_2$) is produced at the counter electrodes (not shown) in the sensor circuit. A different electrolyte may be used in order to generate a specific test gas. For example, a mixture of potassium bisulphate, sulphur and water may he employed for electrolytic generation of Hydrogen Sulphide ($H_2S$). The electrodes are either in contact with a common electrolyte, or with separate electrolytes for the sensing and test circuits.

Referring again to FIG. 2a, counter electrode 48, sensing electrode 24, and reference electrode 47 are known as sensor cell electrodes. Gas generating (or test) electrode 22 and counter electrode 50 are known as test cell electrodes. Sensor cell electrodes 48, 24 and 47 may be operated using a potentiostat circuit, as described below. The sensor cell electrodes and the test cell electrodes may be operated using separate sources of voltage, as shown in the circuit diagrams FIGS. 4, 4a, 5 and 5a, are using a capacitor circuit as shown in FIG. 6. Alternative electrode arrangements are depicted in FIGS. 7, 7a, 8 and 8a.

A test cell counter electrode 50 is coupled in a circuit with test electrode 22, with a switch 100 and a source of potential 108. In an alternative circuit, sensor cell counter electrode 48, reference electrode 47, and sensor electrode 24 are operated by a potentiostat circuit having a source of potential 102. In operation, switch 100 may be closed to enable generation of a test gas.

Figure 5:
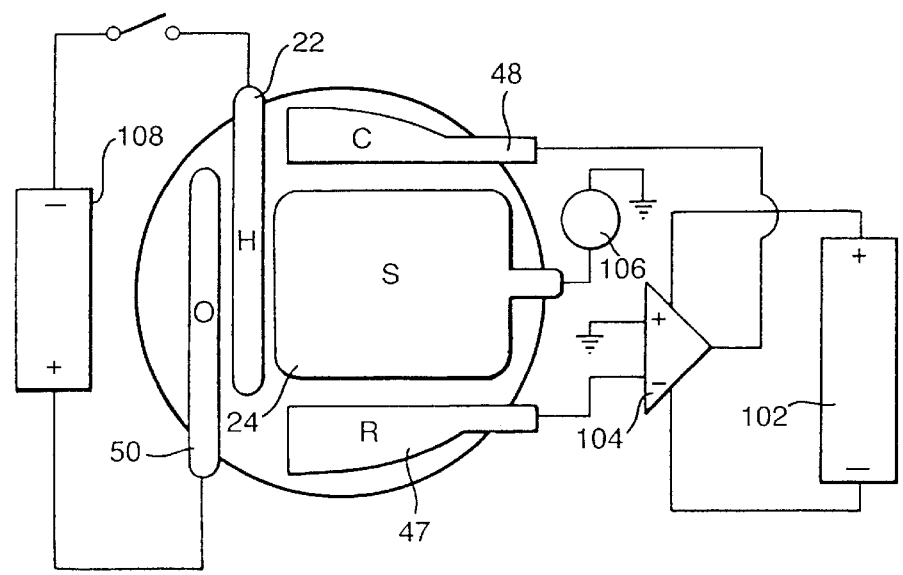
Figure 5A:
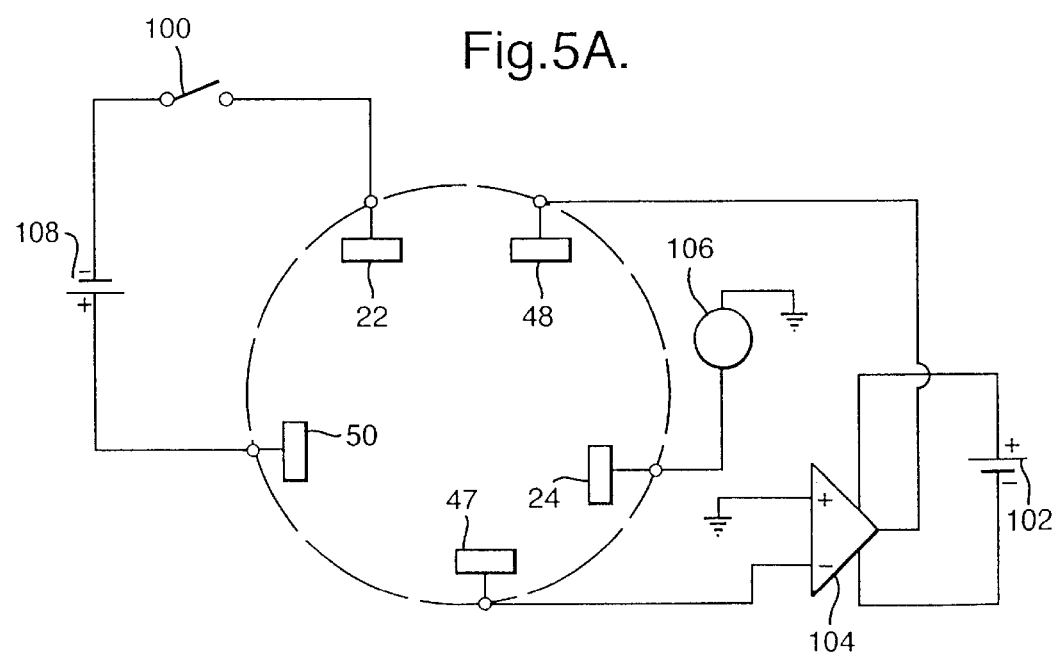
Figure 6:
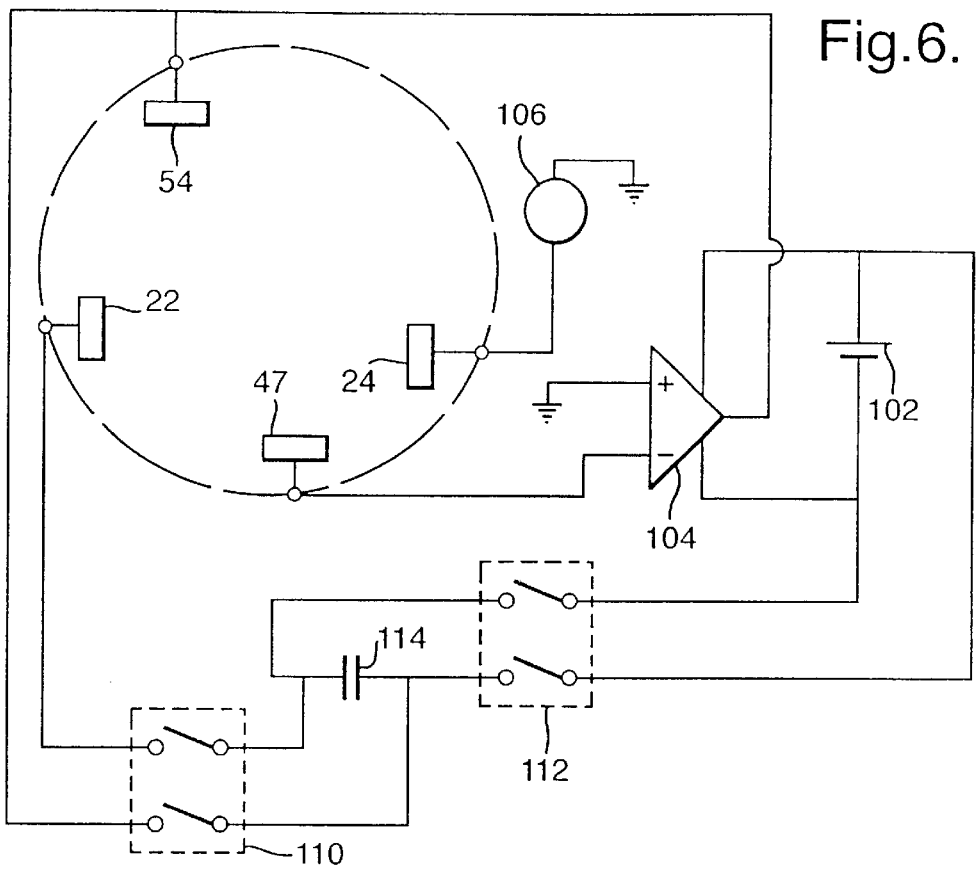

The electrode configuration shown in FIG. 3, and the circuit shown in the circuit diagram of FIG. 5A, may be employed in an alternative embodiment of the invention The use of separate voltage sources 100 and 102 prevents unwanted current passing between the gas generation cell and the sensor electrodes. If a common power supply is used, on operation of the gas generation cell. current is driven through the sensor electrode. Any such electric current would appear indistinguishable from the sensor current. Gas generation electrode 22 and test cell counter electrode 50 are positioned so that the current path between the sensor cell electrodes and the gas generation cell electrodes does not flow to or from the region occupied by the sensor cell electrodes.

In further embodiment of the invention, a common counter electrode 54 for both the test and sensor cells is provided. This arrangement of the electrodes (FIG. 2) minimizes interference between current flowing in the sensor cell and the gas generation cell. Gas sensor 10b incorporating a common counter electrode may be operated with circuits depicted in FIGS. 4 or 6.

Figure 4:
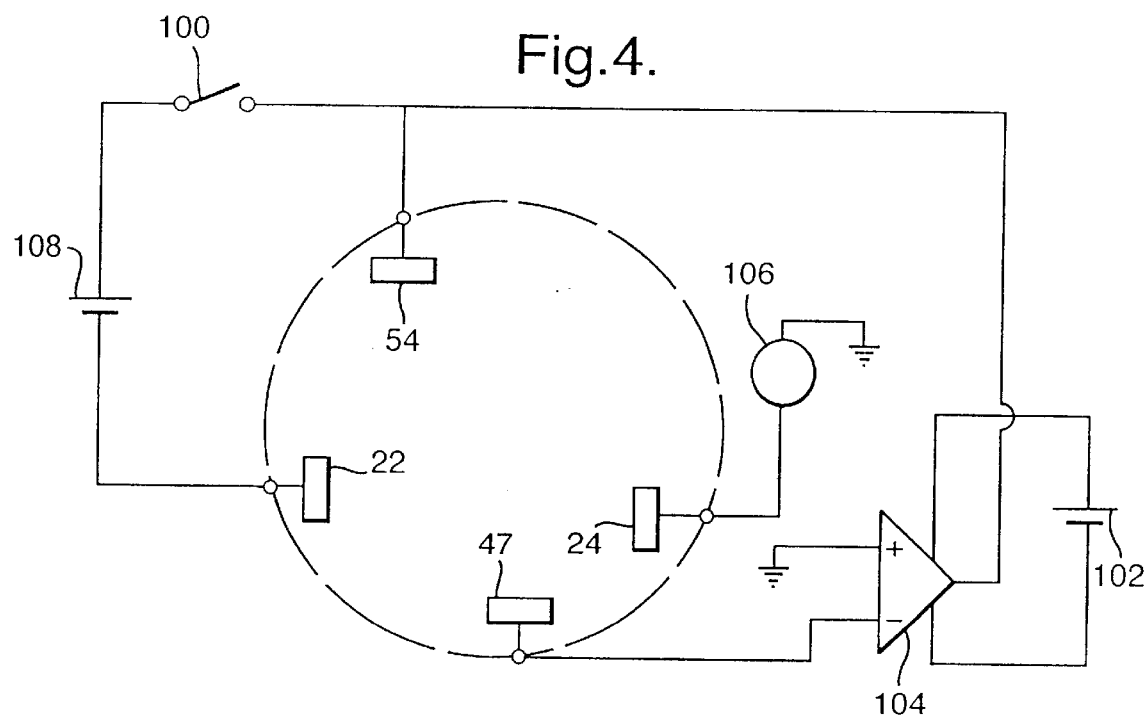
Figure 4A:
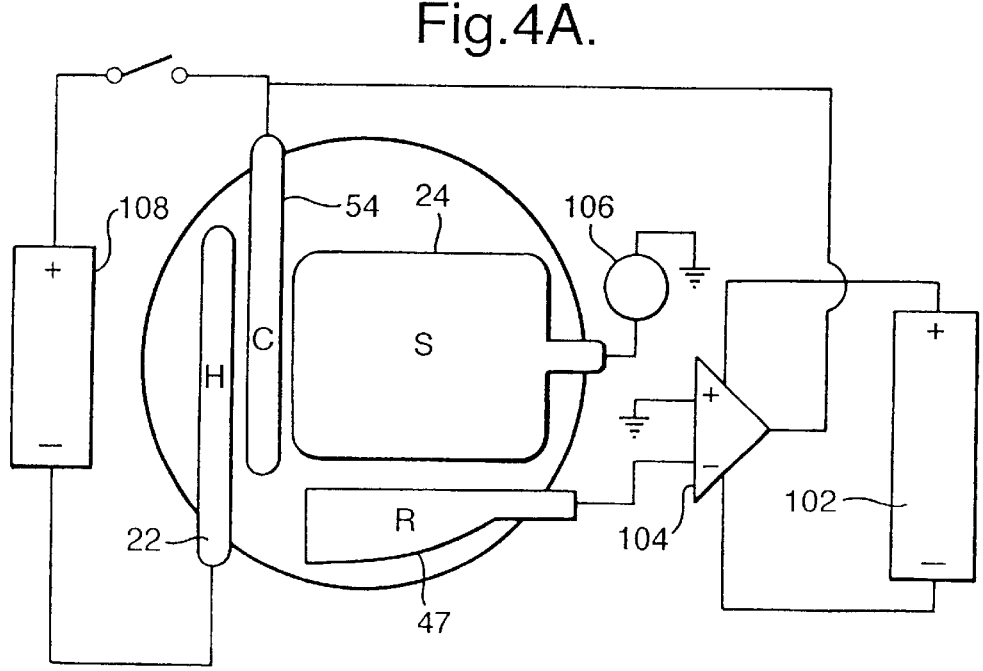

In the circuit diagram of FIGS. 4 and 4A, common counter electrode 54 is coupled with test electrode 22, with a switch 100 and a source of potential 108. Common counter electrode 54 is also coupled with sensor electrode 24 and reference electrode 47. Electrodes. 54, 24 and 47 are operated by a potentiostat circuit, driven by a source of potential 102. In operation, switch 100 is closed to enable generation of a test gas.

Figure 6A:
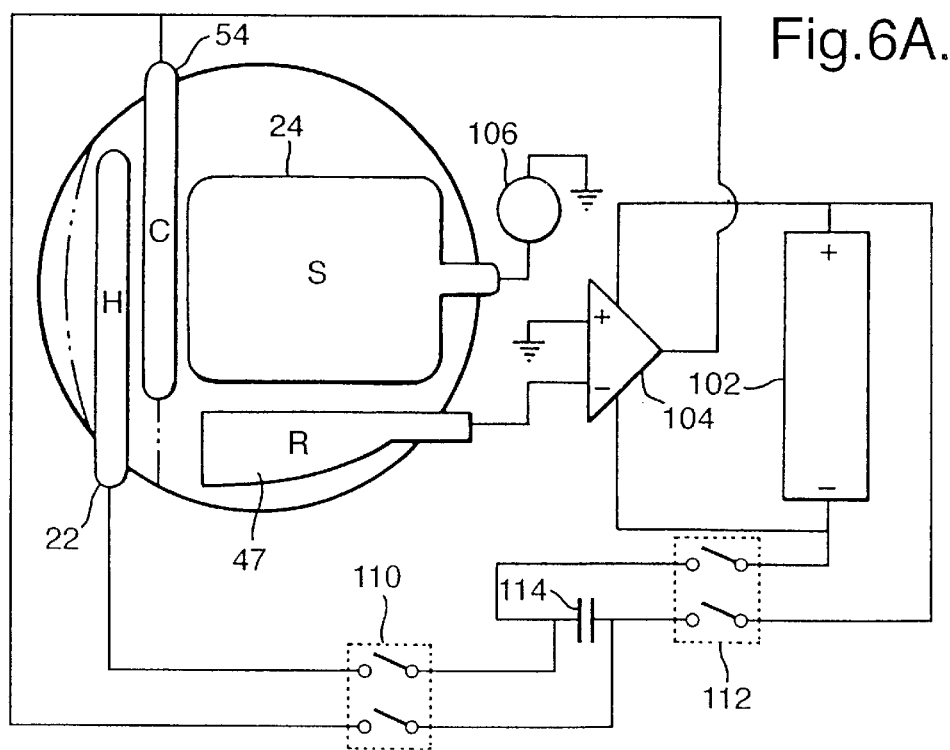
Figure 7:
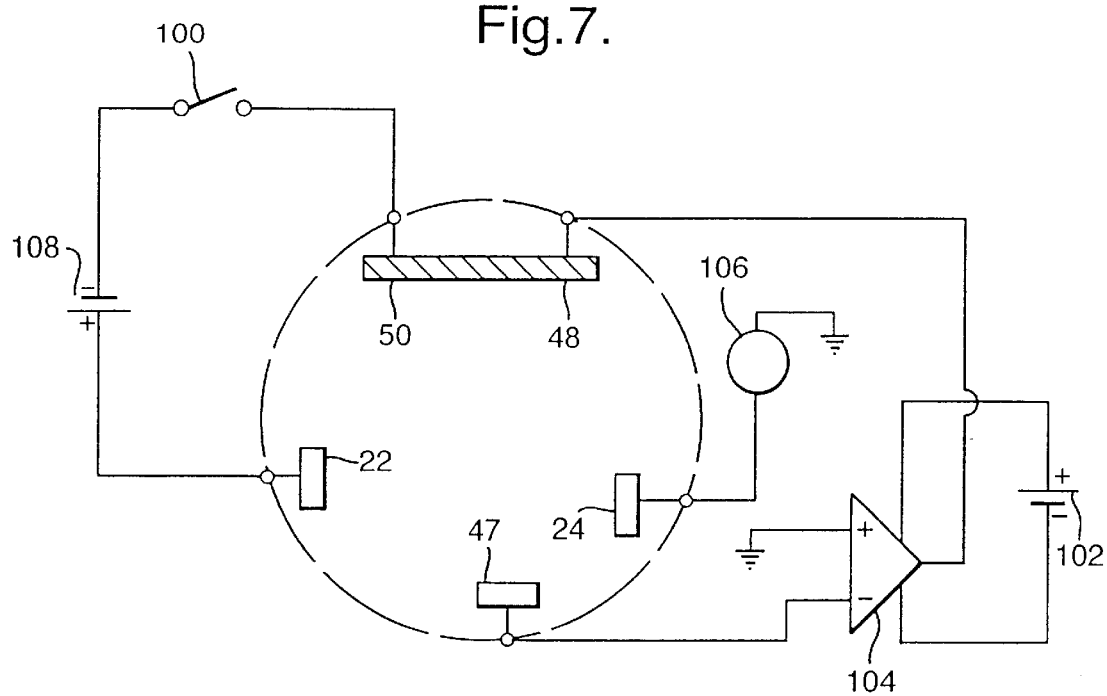
Figure 8:
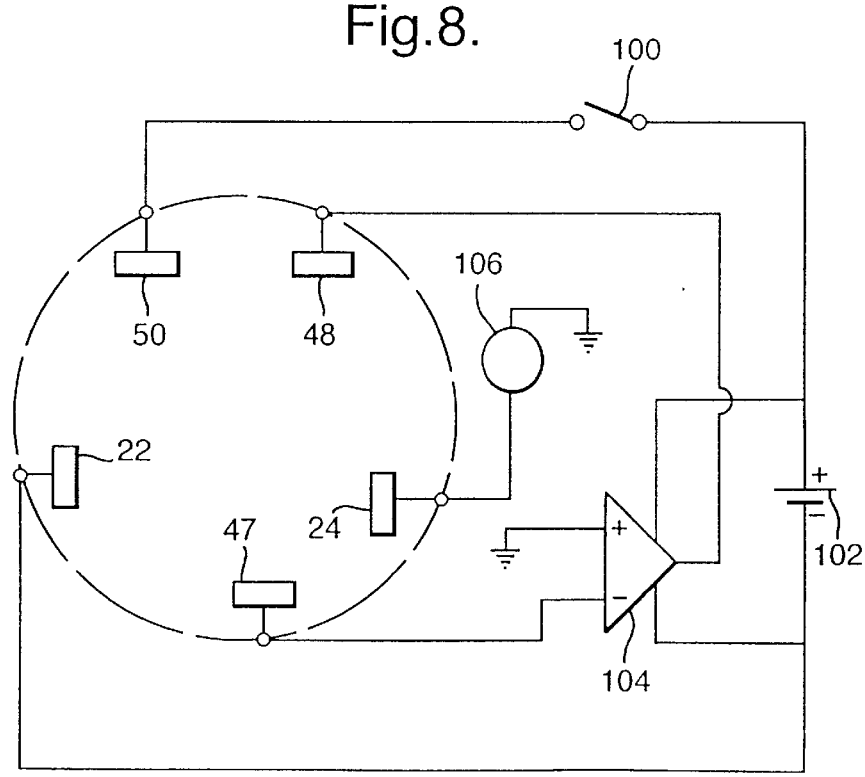
Figure 7A:
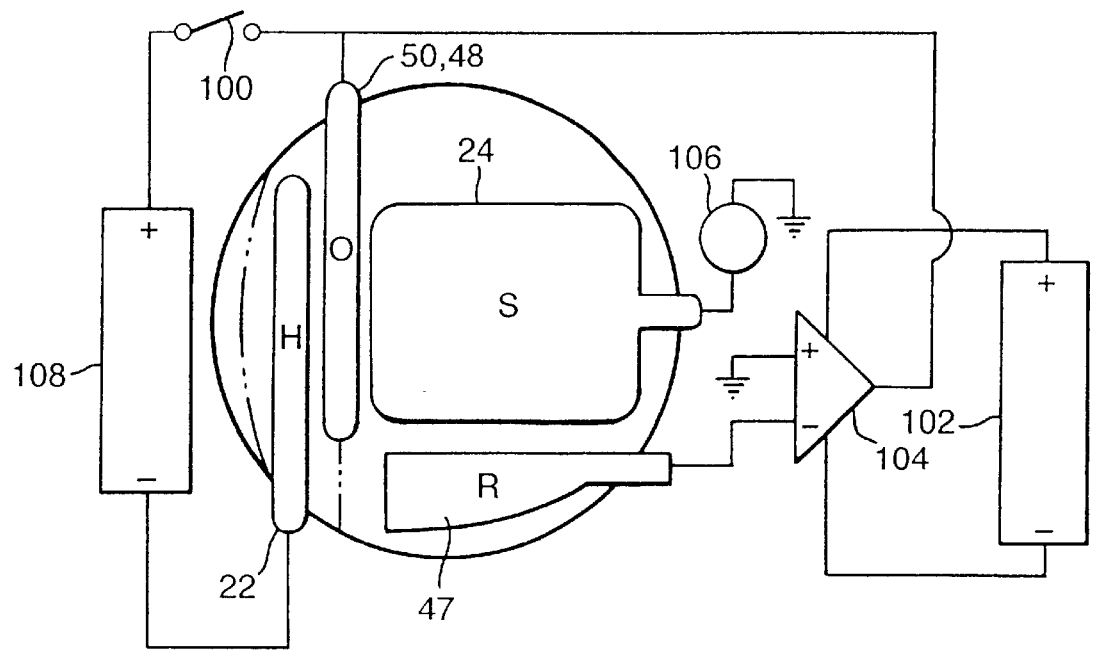
Figure 8A:
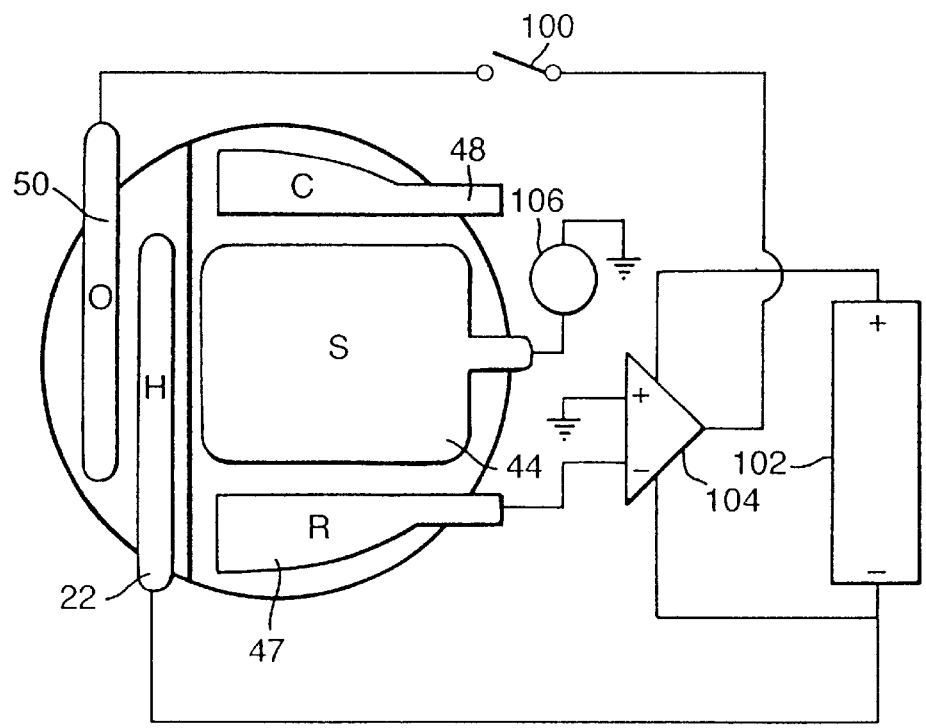

In FIG. 6 and 6A, common counter electrode 54 is coupled with reference electrode 47 and sensor electrode 24. Electrodes 54, 47 and 24 are operated by a potentiostat circuit, driven by a source of potential 102. Common counter electrode 54 is also coupled with test electrode 22 in a further circuit. The further circuit is connected to power supply 102 by a capacitor and switching arrangement, used to supply a pulse of current to the test cell. To minimize electrical interference with the sensor when operating the gas generation cell, the capacitor charging switch connections 112 Is opened before the capacitor discharge switch connections 110 are closed.

FIG. 9 shows a sketch of a cross-sectional view of a gas sensor 10c, having an electrode configuration shown in FIG. 2, and driven by the either the circuit shown in FIGS. 4 or 6. Gas sensor 10c has a barrier 58 positioned so as to cover test electrode 22 and part of common counter electrode 54. Barrier 58 is formed from a membrane, allowing the passage of electrolyte to the electrodes.

To assemble the structures shown in FIGS. 1 or 9 the membrane 20 is positioned over the top of the body 26. Heat and pressure are applied to the areas A (See FIG. 14) by means of a press tool (not shown) in order to compress the substrate and the electrodes 22 and 24 onto the upper surface of body 26, so that the substrate is securely fixed to the top of the housing. During compression, the composite located in recesses 30 molds itself around the heads of the terminal pins 28 to give a good electrical connection between the pins 28 and the electrodes.

Referring now to FIG. 14, this shows an embodiment of gas sensor employing the embodiments of the invention described below. A gas sensor comprises an electrochemical gas sensor 2 in the form of a two part housing, namely a body 4 which is generally cylindrical (with a hollow interior 6 for forming an electrolyte reservoir), and a disc-shaped cap member 8. Electrical terminal pins 10 of nickel or tinned copper, have heads 14. Pins 10 are located in recesses 16 in the top portion of body 4. A porous flexible substrate 20, in the form of a disc, is disposed on upper surface of body 4. Electrodes 22, 24 formed from a mixture of electrically conductive catalyst particles in a PTFE binder, are screen printed or filter deposited onto a lower surface of substrate 20 in the form of segments. A small amount of conductive polymer/carbon composite 26 is placed in recesses 16 over each contact pin head 14. Cap member 8 has through holes 28 drilled therein to a recessed manifold area 30 for permitting atmospheric gas to diffuse through apertures 28 and thence, via manifold area 30, through substrate 20 to electrode 22. Electrolyte (not shown) within electrolyte recess or reservoir 6 is maintained in contact with electrodes 22, 24 by means of a wick material or porous structure 31, according to the present invention. The invention is described, in detail, with reference to FIGS. 15 and 16, below.

To assemble the sensor base of body 4 electrical terminal contact pins 10 are located therein with conductive polymer or composite 26 positioned within recesses 16 over the heads 14. The substrate 20 is placed across the top of cylindrical body 4. Heat and pressure is applied in the areas A (shown by double headed arrows) by means of a press tool (not shown), in order to compress and bond the substrate 20 and the electrodes 22. 24 onto upper surface of body 4. The conductive polymer or composite 26 bonds together the arrangement so the electrode 20 is electrically connected to the top of the body 4. Compression of the electrodes 22, 24 and the substrate 20 in the area A, together with the impregnation into the porous substrate 20 of the housing, and the conductive polymer or composite 26, ensures that substrate 20 and electrodes 22, 24 are sealed to prevent ingression of electrolyte into the regions of the electrical connections. Simultaneously, composite 26 moulds itself around the heads 14 of the terminal pins 10, thereby ensuring a good electrical connection between the contact pins and the electrodes 22, 24.

FIG. 15 shows an example of an electrode (hereinafter referred to as an electrode assembly) fabricated in accordance with the invention. The electrode assembly 22, 24, as described above with reference to FIG. 10, comprises a porous substrate 50, permeable to gas but not to electrolyte. There is deposited on the substrate 50 an electrode layer 52 which is a mixture of binder particles of catalyst, such as platinum and another material; for example PTFE which acts as a polymeric binder. A glass fiber wick 54 is placed over the electrode material 52 when it is still wet and urged against the material 52. The electrode material 52 is then allowed to dry in air for approximately 1 hour at room temperature. The electrode assembly 22, 24 is then sintered at a temperature between 300° C. and 370° C. for approximately 1 hour. These conditions fuse the binder particles, to the substrate and to the wick, whilst still ensuring a porous structure is defined by the wick.

The electrode assembly 22, 24 and the properties of the wick material 54 are carefully chosen to give good gas access through the substrate and electrode, electrolyte access through the wick 54 to the electrode 52, and good physical adhesion of each layer one to another.

The wick material 54 may be in the form of a disc 56 covering substantially all the electrode 52, or it may have tails or extensions 58 stretching above the plane of the electrode 52 or outside its area in the same plane in order to communicate with a remote electrolyte reservoir (not shown).

Wick material 54 may be flexible or rigid, with shaped extensions to fit a fuel cell (not shown) or electrochemical cell (not shown). Printing of conductive inks or other metal catalysts may occur at this time and the ink or catalyst may be cured by the same heat treating process used to sinter the electrode assembly 22, 24.

The wick material 54 may be impregnated with gelled or other dry or a partially dry form of electrolyte at a region where it contacts the electrolyte or where it contacts the electrode layer 52. The electrolyte may then hydrate on exposure to a moist atmosphere, thereby avoiding the need for filling the cell with more dilute electrolyte during assembly. The porous structure may be dimensioned and arranged so that it comprises different layers or regions of differing porosity, so that layers close to the surface of the electrode have a greater affinity to the electrolyte than those layers further from the electrode surface. This enhances the wicking effect and ensures the electrode surface is always wetted by electrolyte.

In certain cases it may be advantageous to allow limited gas access from a gas space at the rear side of the electrode assembly 22, 24 to the front side of the electrode assembly 22, 24. This allows gas pressure equalization across two faces of the electrode assembly 22, 24. To ensure free passage, the wick material can be treated to make it hydrophobic in a small area, and the wick may then be firmly attached to the electrode as described. The treated area of wick remains depleted of electrolyte, and no film of electrolyte can form between the wick and the electrode in this area, thus leaving a passage for gas flow substantially unobstructed.

In the embodiment of electrode assembly 22A shown in FIG. 15 a second electrode is connected to an available surface of the wick 54, effectively "sandwiching" the wick 54 between two electrodes. This maximizes the amount of electrolyte in contact with electrodes.

FIG. 13 shows a sensor electrode comprising a layer of electrode material deposited onto a gas permeable substrate 12 (such as for example PTFE) which is non-permeable to the electrolyte. The electrode material 8 is located on the side of the substrate 12 remote from the diffusion barrier 5. The electrode 8 is basically a disc of electrically conductive material with two tabs which define regions where electrical contact can be made. The electrode 8 is made up of a mixture of catalyst particles, electrically conductive material (such as an electrically conductive ink) and a polymeric binder, suspended in a medium such as for example which aids the deposition, and is printed on to the substrate 12 using a printing technique.

A glass fiber wick material 13 is placed over the electrode 8 while the electrode material is still wet. The wick has two cut-outs 14 which align with holes 15 in the substrate.

The electrodes 9 and 10 are provided on the inner face of a second gas permeable substrate 16, for example PTFE, which is non-permeable to electrolyte. The electrode materials are deposited on the substrate 16 by a printing method in the same way as that used to make electrode 8, and each electrode 9, 10 has an a tab formed at a position aligned with one of the holes 16.

FIG. 10 shows a further embodiment in which the sensor 1 comprises a plastics housing 2 made of two parts, namely a cylindrical body 3 having a central recess 4 which forms a reservoir for an electrolyte, and diffusion barrier 5. The upper part of the housing has a cavity in which is located an electrode assembly 6. The diffusion barrier 5 has a central recess 5a which, in use, defines a small space above the electrode assembly 6 and has a small aperture 7 through which ambient air may pass into the space defined by the recess 5a.

The electrode assembly comprises basically three electrodes; a sensing electrode 8, a counter electrode 9 and a gas generator electrode 10. The electrodes are best seen in FIG. 11.

FIG. 11 shows a sensor electrode which comprises a layer of electrode material deposited onto a gas permeable substrate 12 (such as for example PTFE) which is non-permeable to the electrolyte. The electrode material 8 is located on the side of the substrate 12 remote from the diffusion barrier 5. The electrode 8 is basically a disc of electrically conductive material with two tabs which define regions where electrical contact can be made. The electrode 8 is made up of a mixture of catalyst particles, electrically conductive material (such as an electrically conductive ink) and a polymeric binder, suspended in a medium such as for example which aids the deposition, and is printed on to the substrate 12 using a printing technique.

A glass fiber wick material 13 is placed over the electrode 8 while the electrode material is still wet. The wick has two cut-outs 14 which align with conductor tracks 15 on the substrate. The conductor tracks may be of the same material as the electrodes, or a different material.

The electrodes 9 and 10 are provided on the inner face of a second gas permeable substrate 16, for example PTFE, which is non-permeable to electrolyte. The electrode materials are deposited on the substrate 16 by a printing method in the same way as that used to make electrode 8.

The layered electrode assembly 6 is assembled whilst the electrode materials 8, 9 and 10 are still wet, and the assembly 6 is pressed and sintered to form an integral sandwich which causes the binders, the electrode materials, 8, 9 and 10 the substrates 12, 16 and wick 13 to fuse together. Electrodes 9 and 10 fuse via to cut-outs 14 to the conductor tracks. Alternatively, discs 20 of conductive polymer, (15a, 15b) might be included between electrodes 9 and 10 and conductor tracks 15a and 15b during the sintering process, or following it in a separate process, in order to aid the electrical connection. The final product is a generally planar electrode assembly. The electrode assembly 6 is positioned in the housing 2 with the substrate 12 which carries the sensing electrode 8 facing the diffusion barrier 5.

Spaced around a common pitch circle diameter are three electrical contact pins 17. One of the pins 17 makes contact with one of the tabs on the electrode 8, one makes contact with conductor track 15a connected to electrode 9, and the other pin 17 contacts conductor track 15b, connected to electrode 10. The pins 17 may be protected against electrolytic corrosion by the electrolyte by the provision of an electrically conductive polymer layers 18 between the terminal pin 17 and the electrode 8 or conductor tracks 15a and 15b.

In the embodiment shown in FIG. 10 the wick 13 contacts a cylindrical wick 13(a) which is located in the cavity of housing 3. Alternatively, the wick 13 may have tails or extensions which communicate with electrolyte contained within the cavity 4 of housing 3. The wick could be flexible or rigid with shaped extension pieces to fit the sensor design.

Electrolyte in the cavity of the housing is transported by capillary action through the wick 13 to the electrodes 8, 9 and 10. The wick 13 may have graded porosity or may be made of layers of wick material which provide different degrees of porosity. The wick 13 may be designed so that layers of the wick 13 closest to the electrodes 8, 9, 10 have a greater affinity for the electrolyte than the layer or layers further from the electrodes. In this way, if the electrolyte dries out so that it does not saturate the entire wick, the remaining electrolyte will lie preferentially in those layers closest to the electrodes.

The wick 13 could be impregnated with gelled, dry or partially dry electrolyte prior to joining the wick to the electrodes 8, 9, 10.

The advantages of the above method of assembly of electrodes is that the contact between the pins 17 and the electrodes 9, 10 is simplified and made more reliable because the electrode 8 on the first substrate 12 is connected to the first substrate and the respective pin 17 by the electrically conductive polymer 20. Furthermore the whole area of the substrate 12 is covered by the electrode 8, thus allowing the diameter cells to be reduced for a given activity of the electrode and hence improvement of the useful lifetime of the cell. In addition the whole assembly is more robust and all electrodes are in good contact directly with the wick material. By using a single planar assembly 6 which can be sealed into a blind housing the number of components are effectively reduced and hence cheaper detectors can be built.

In certain cases it is advantageous to allow limited gas access from a gas space at one side of the electrode assembly to a gas space on the other side of the electrode assembly. This allows pressure equalization between the two sides of the cell. The presence of electrolyte covering the electrodes 8, 9 and 10 will inhibit or prevent gas flow. To ensure free passage of gas through the wick 13, the wick material can be treated to make it hydrophobic in one or more localized small regions. The treated area of the wick remains empty of electrolyte, and no film of electrolyte can form between the wick 13 and the electrodes 8, 9, 10 thus leaving the flow of gases to rear side of the electrodes unobstructed.

In a preferred embodiment of the invention as shown schematically in FIG. 13 two further electrodes 21, 22 are positioned on the same surface as that on which the sensing electrode 8 is placed. The further electrodes comprise a counter electrode 21 and a gas generator electrode 22. Preferably the electrolyte is sulphuric acid and the test gas hydrogen is generated by electrolysis of the electrolyte. In operation an electrical potential is applied between the counter electrode 9 and the gas generator 10 and the test gas is delivered to above the sensing electrode 8 through the porous substrates 12, 16 and wick 13.

The hydrogen test gas is generated by the reaction described in Eqn 1. It is a feature of this reaction that, if the generator electrode 22 has a source of oxygen available, then oxygen is reduced according to Eqn 2. Current flows in parallel with that passed in the $H_2$ generation reaction, and so reduces the operating efficiency of the generator electrode 22. The oxygen reduction reaction will happen particularly with the design of electrode assembly 6 as shown in FIG. 13 and even more so if the electrode material of the generator electrode 22 is an active catalyst such as platinum. The current generated by the oxygen reduction will be large compared with that due to hydrogen generation at low electrode potentials.

In order to improve the efficiency of the sensor, in accordance with one aspect of the invention, the gas generator electrode 22 is made of a material which is, or includes, a poor catalyst for oxygen reduction, and is highly conductive, disperses easily in an ink and generates hydrogen in the presence of oxygen at much lower potential (ie. Lower total current density) than does platinum. An example is $RuO_2$ (Ruthenium dioxide) other materials which are also poor oxygen reduction catalysts are carbon, gold and the metal oxides of tungsten and molybdenum. In contrast, the sensing electrode 8 comprises a good catalyst, such as platinum, for the oxidation of the sensed gas, and is also a good catalyst for the reduction of oxygen.

In a further embodiment of the invention the sensing electrode 8 comprises a multi layer construction where the first layer comprises a layer of conductive ink, such as $RuO_2$ ink, and a top layer of platinum ink. This latter construction improves conductivity and reduces cost because of the use of cheaper ink. The conductive ink layer might form the electrically conductive pathway between an electrode in the inner cavity of the sensor and the external contact 17, as shown in FIG. 10.

In a further embodiment of the invention the porosity of the substrate 12 on which the gas generator electrode 22 is provided, may be reduced, hut not to such an extent to inhibit the emission of $H_2$. This could be achieved, for example, by hot pressing the substrate 12 in the vicinity of the gas generator electrode 22 and partially blocking the pores of the substrate 12 with a PTFE (polyfluroethene) or other blocking substance, or by sealing, partially or completely, a low porosity material over the substrate 12 in the vicinity of the electrode 22.

As an alternative, the porosity and/or the wettability of the generator electrode 22 may be reduced, though not to such a degree as to inhibit the generation of $H_2$. This could be achieved, for example, by hot pressing the electrode 22, and/or incorporating into the electrode 22 less hydrophobic, or more hydrophilic materials—examples of such hydrophobic materials are metal oxides and less hydrophilic materials are PTFE or polypropylene.

Solid polymer electrolytes (SPE) are becoming increasingly more available. SPE's adhere to electrodes and accordingly ensure that there is a conductive path always present between the electrodes.

The invention has been described by way of examples only and variation may be made to them without departing from the scope of the invention. For example, different aspects of the embodiments may be combined together so as to form new embodiments which are within the scope of the invention.

What is claimed is:

1. A gas sensor, comprising:
   a housing having a diffusion barrier through which ambient gas to be detected may pass and in which there is located a sensing electrode;
   a counter electrode;
   an optional reference electrode; and
   an electrolyte in contact with said electrodes;
   a cell operable in a sensing mode where electrical potentials are applied to said counter electrode and said sensing electrode to effect electrolysis of ambient gases that reach said sensing electrode and thereby produce an electrical current indicative of a concentration of said gas being detected;
   wherein at least one of said electrodes consisting of a layer deposited on a gas permeable substrate, said layer comprising a mixture of electrically conductive catalyst particles and binder particles and being in contact with and covered by a porous wick which conveys electrolyte to said electrodes; and wherein said wick and said gas permeable substrate and at least one of said electrodes being heat-bonded together such that the binder particles in at least one of said electrodes are fused to said gas permeable substrate and said wick.

2. The gas sensor according to claim 1, wherein:

at least one of said electrodes is deposited on a first gas permeable substrate and at least one of said electrodes is deposited on a second gas permeable substrate arranged to face said first permeable substrate, and said wick is placed between said first permeable substrate and said second permeable substrate such that heat-bonding fuses said first permeable substrate and said second permeable substrate to opposite sides of said wick, thereby providing a unitary electrode/wick assembly.

3. The gas sensor according to claim 2, further comprising:

a gas generator electrode for generating a self-test gas for detection by said sensing electrode in a further self-test mode, said gas generator electrode and said sensing electrode being mounted on a same gas permeable substrate.

4. The gas sensor according to claim 3, wherein:

said gas generator electrode comprises a material from the group comprising at least one of ruthenium dioxide, gold, carbon, tungsten oxide and molybdenum oxide.

5. The gas sensor according to claim 3, wherein:

an electrical potential is applied between said gas generator electrode and said counter electrode producing hydrogen as a test gas, and regions of said gas permeable substrate in a vicinity of said gas generator electrode are modified to inhibit a reduction of oxygen without inhibiting the generation of hydrogen.

6. The gas sensor according to claim 5, wherein:

said regions of said gas permeable substrate are modified by incorporating a blocking substance within pores of said gas permeable substrate.

7. The gas sensor according to claim 3, wherein:

said gas generator electrode is porous.

8. The gas sensor according to claim 3, further comprising:

a sensor cell and a test cell arranged to generate a test gas on demand and a test gas pathway for directing said test gas such that said test gas is detected by the sensor cell, thereby verifying that said gas sensor is functioning; and a baffle disposed between said gas sensor and said test cell so as to prevent electrical interference therebetween.

9. The gas sensor according to claim 3, wherein:

said gas generator electrode and a common electrode act as a first pair of electrodes to generate a test gas and said common electrode and said sensing electrode act as a second pair of electrodes to sense gas; and said gas sensor further comprising an isolator for isolating said first pair of electrodes from said second pair of electrodes from one another so that only one pair of electrodes is operational at any instant.

10. The gas sensor according to claim 9, wherein:

a capacitor to discharge through a test circuit when a sensing circuit is disconnected from a current source.

11. The gas sensor according to claim 1, wherein:

said wick comprises a sheet of glass fiber material.

12. The gas sensor according to claim 1, wherein:

said wick has a graded porosity and is constructed and arranged to improve electrolyte flow in a vicinity of at least one of said electrodes compared to regions of said wick spaced from at least one of said electrodes.

13. The gas sensor according to claim 1, further comprising:

a gas generator electrode for generating a self-test gas for detection by said sensing electrode in a further self-test mode.

14. The gas sensor according to claims 13, wherein:

said gas generator electrode comprises a material from the group comprising at least one of ruthenium dioxide, gold, carbon, tungsten oxide and molybdenum oxide.

15. The gas sensor according to claim 13, wherein:

an electrical potential is applied between said gas generator electrode and said counter electrode producing hydrogen as a test gas, and regions of said gas permeable substrate in a vicinity of said gas generator electrode are modified to inhibit a reduction of oxygen without inhibiting the generation of hydrogen.

16. The gas sensor according to claim 15, wherein:

said regions of said gas permeable substrate are modified by incorporating a blocking substance within pores of said gas permeable substrate.

17. The gas sensor according to claim 6, wherein:

said blocking substance comprises a plastic material.

18. The gas sensor according to claim 13, wherein:

said gas generator electrode is porous.

19. The gas sensor according to claim 18, wherein:

said porous gas generator has an available source of oxygen; and said porous gas generator electrode comprises a poor catalyst for oxygen reduction, and is adapted to reduce at least one of porosity and wettability of said gas generator electrode without inhibiting generation of hydrogen.

20. The gas sensor according to claim 13, further comprising:

a sensor cell and a test cell arranged to generate a test gas on demand and a test gas pathway for directing said test gas such that said test gas is detected by the sensor cell, thereby verifying that said gas sensor is functioning; and a baffle disposed between said gas sensor and said test cell so as to prevent electrical interference therebetween.

21. The gas sensor according to claim 20, wherein:

said baffle comprises a gas permeable membrane.

22. The gas sensor according to claim 20, wherein:

said baffle is arranged between respective sensor and generator electrolytes.

23. The gas sensor according to claim 13, wherein:

said gas generator electrode and a common electrode act as a first pair of electrodes to generate a test gas and said common electrode and said sensing electrode act as a second pair of electrodes to sense gas; and said gas sensor further comprising an isolator for isolating said first pair of electrodes from said second pair of electrodes from one another so that only one pair of electrodes is operational at any instant.

24. The gas sensor according to claim 23, further comprising:

a capacitor to discharge through a test circuit when a sensing circuit is disconnected from a current source.

25. The gas sensor according to claim 24, further comprising:

a switching for switching a current source into a test circuit and simultaneously isolating a current source from a sensing circuit.

26. The gas sensor according to claim 1, wherein:

said electrolyte comprises a solid polymer.

27. The gas sensor according to claim 1, wherein:

said wick is adapted to be hydrophobic in one or more areas to provide areas depleted of electrolyte, thereby allowing gas to pass through said wick to equalize gas pressures on either side of said wick.

28. A method of manufacturing an electrode assembly for a gas sensor comprising:

depositing a first electrode material comprising a mixture of electrically conductive catalyst particles and binder particles on a first gas permeable substrate to form a sensing electrode;

depositing a second electrode material comprising a mixture of electrically conductive catalyst particles and binder particles on a second gas permeable substrate to form a counter electrode;

depositing a third electrode material comprising a mixture of electrically conductive catalyst particles and binder particles on one of said gas permeable substrates to form a gas generator electrode;

providing a porous wick between and in mutual contact with said sensing electrode, said counter electrode and said gas generator electrode and between the first and second substrates, said porous wick being provided to contain said electrolyte during use; and heat-bonding said porous wick, at least one of said gas permeable substrates and at least one of said electrode together such that said binder particles in at least one of said electrodes are fused to said gas permeable substrate and said wick, thereby forming a unitary electrode/wick assembly.

* * * * *